US009932563B2

United States Patent
(12) United States Patent
Williams et al.

(10) Patent No.: US 9,932,563 B2
(45) Date of Patent: Apr. 3, 2018

(54) COMPOSITIONS AND METHODS FOR INHIBITING GENE EXPRESSIONS

(71) Applicant: GEORGIA TECH RESEARCH CORPORATION, Atlanta, GA (US)

(72) Inventors: Loren D. Williams, Atlanta, GA (US); Po-Yu Fang, Atlanta, GA (US); Chiaolong Hsiao, Atlanta, GA (US); Justin Williams, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/911,645

(22) PCT Filed: Sep. 11, 2014

(86) PCT No.: PCT/US2014/055149
§ 371 (c)(1),
(2) Date: Feb. 11, 2016

(87) PCT Pub. No.: WO2015/038746
PCT Pub. Date: Mar. 19, 2015

(65) Prior Publication Data

US 2016/0194613 A1 Jul. 7, 2016

Related U.S. Application Data

(60) Provisional application No. 61/876,450, filed on Sep. 11, 2013.

(51) Int. Cl.

| | |
|---|---|
| ***C12N 15/11*** | (2006.01) |
| ***C12N 7/00*** | (2006.01) |
| ***C12N 15/88*** | (2006.01) |
| ***A01N 57/16*** | (2006.01) |
| ***C12N 15/113*** | (2010.01) |
| *C12N 15/86* | (2006.01) |

(52) U.S. Cl.
CPC ............... *C12N 7/00* (2013.01); *A01N 57/16* (2013.01); *C12N 15/1137* (2013.01); *C12N 15/88* (2013.01); *C12N 15/86* (2013.01); *C12N 2310/14* (2013.01); *C12N 2795/18123* (2013.01); *C12N 2795/18142* (2013.01); *C12N 2795/18151* (2013.01); *C12N 2795/18152* (2013.01)

(58) Field of Classification Search
CPC .............................. C12N 7/00; C12N 15/1137
See application file for complete search history.

(56) References Cited

U.S. PATENT DOCUMENTS

2013/0167267 A1* 6/2013 Arhancet ............. C07K 14/005 800/298
2016/0177299 A1* 6/2016 Arhancet ............... A61K 48/00 435/91.32

FOREIGN PATENT DOCUMENTS

| | | |
|---|---|---|
| WO | 2007068747 | 6/2007 |
| WO | 2010047839 | 4/2010 |
| WO | 2011116226 | 9/2011 |

OTHER PUBLICATIONS

Cadena-Nava et al. Journal of Viriology p. 3318-3326, 2011.*
Naskalska et al. Polish Journal of Micorbiology 2015, 64, 3-13.*
Seow et al. Molecular Therapy 17, 767-777, 2009.*
Bhaumik et al. Oncogene 2008, 27, 5643-5647.*
Fiedler et al. Angew Chem Int Ed Engl Dec. 2010 49:9648-9651.*
Agrawal, et al., RNA interference: biology, mechanism, and applications, Microbiol Mol Biol Rev., pp. 67(4):657 85 (2003).
Beekwilder, et al., Secondary structure model for the last two domains of single-stranded RNA phage Q beta, J Mol Biol., 247(5):903-17 (1995).
Bowman, et al., Preparation of long templates for RNA in vitro transcription by recursive PCR, Methods Mol Biol., 941:19-41 (2012).
Galaway and Stockley, MS2 viruslike particles: a robust, semisynthetic targeted drug delivery platform, Mol Pharm., 10(1):59-68 (2013).
Huvenne and Smagghe, Mechanisms of dsrna uptake in insects and potential of rnai for pest control: A review , J Insect Physiol., 56:227-35 (2010).
Lau, et al., Evolution and protein packaging of small molecule RNA aptamers , ACS Nano, 5:7722-9 (2011).
Milhavet, et al., RNA interference in biology and medicine, Pharmacol Rev., 55: 629-648 (2003).
Oey, et al., Rnai knock-down of lhcbm1, 2 and 3 increases photosynthetic h2 production efficiency of the green alga Chlamydomonas reinhardtii, PLoS One, 8:e61375 (2013).
Pan, et al., Development of a microrna delivery system based on bacteriophage ms2 virus-like particles , FEBS J, 279:1198-1208 (2012).
Rhee, et al., Colorful virus-like particles:Fluorescent protein packaging by the q beta capsid, Biomacromolecules, 12:3977-81 (2011).
Schneider, et al., Selection of high affinity RNA ligands to the bacteriophage R17 coat protein, J Mol Biol, 228(3):862-9 (1992).
Sledz and Williams, RNA interference in biology and disease, Blood, 106 (3):787-94 (2005).
Smith, et al., Reengineering viruses and virus-like particles through chemical functionalization strategies , Curr Opin Biotechnol, 24(4):620-6 (2013).

(Continued)

*Primary Examiner* — Brian A Whiteman
(74) *Attorney, Agent, or Firm* — Smith, Gambrell & Russell, LLP

(57) ABSTRACT

A combined packing and assembly method that efficiently packs ribonucleic acid (RNA) into virus like particles (VLPs) has been developed. The VLPs can spontaneously assemble and load RNA in vivo, efficiently packaging specifically designed RNAs at high densities and with high purity. In some embodiments the RNA is capable of interference activity, or is a precursor of a RNA capable of causing interference activity. Compositions and methods for the efficient expression, production and purification of VLP-RNAs are provided. VLP-RNAs can be used for the storage of RNA for long periods, and provide the ability to deliver RNA in stable form that is readily taken up by cells.

13 Claims, 7 Drawing Sheets

(56) References Cited

OTHER PUBLICATIONS

Whitehead, et al., Knocking down barriers: Advances in sirna delivery ,. Nat Rev Drug Discov., 8: 129-38 (2009).
Witherell and Uhlenbeck, Specific RNA binding by q beta coat protein, Biochemistry; 28: 71-6 (1989).
Zeltins, Construction and characterization of virus-like particles: A review , Mol Biotechnol., 53: 92-107 (2013).
Zeng, et al., MicroRNAs and small interfering RNAs can inhibit mRNA expression by similar mechanisms, PNAS, 100:9779-84 (2003).
Zhou, et al., RNA interference in the termite Reticulitermes flavipes through ingestion of double-stranded RNA , Insect Biochem Mol Biol., 38: 805-15 (2008).
International Search Report for corresponding PCT application PCT/US2014/055149 dated Jan. 8, 2015.

* cited by examiner

Fig. 5A
(A)
Fig. 5B
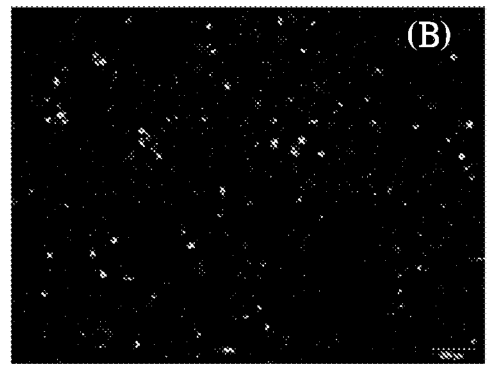
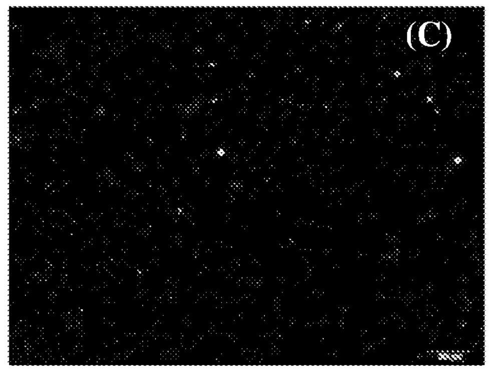
Fig 5C
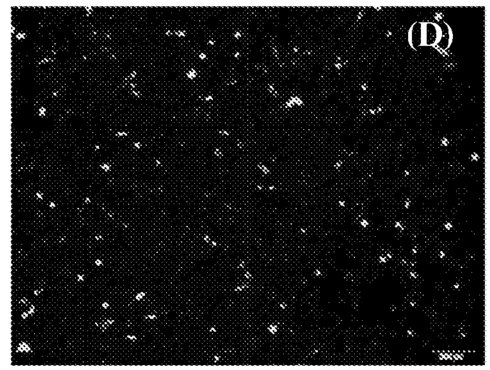
Fig. 5D

COMPOSITIONS AND METHODS FOR INHIBITING GENE EXPRESSIONS

CROSS REFERENCE TO RELATED APPLICATONS:

This application is a 371 application of International Application No. PCT/2014/055149, filed Sep. 11, 2014, which claims priority to and benefit of U.S. Provisional Patent Application No. 61/876,450 filed on Sep. 11, 2013.

STATEMENT REGARDING FEDERALLY SPONSORED RESEARCH OR DEVELOPMENT

This invention was made with Government Support under Agreement NAI awarded to Loren D. Williams by the NASA Astrobiology Institute, Contract number NNA09DA78A. The Government has certain rights in the invention.

REFERENCE TO SEQUENCE LISTING

The sequence listing submitted on Feb. 11, 2016, as a txt file named "GTRC_6427_ST25.txt," created on Sep. 11, 2014, and having a size of 3,575 bytes is hereby incorporated by reference pursuant to 37 C.F.R.§ 1.52(e)(5).

FIELD OF THE INVENTION

The invention relates to the field of RNA interference and in particular to use of virus like particles in iRNA.

BACKGROUND OF THE INVENTION

In RNA interference (RNAi), an iRNA (an RNA molecule with gene interference activity) of appropriate sequence will down-regulate a given gene by preventing a specific messenger RNA (mRNA) from producing protein. RNAi has been rapidly developed into a potent and broadly applied tool in medicine, biofuels, agriculture and basic research (Sledz and Williams, *Blood,* 106(3):787-794 (2005)).

Production, packaging, storage and delivery of RNA remains the central challenge to the therapeutic application of RNAi technology. Purified RNAs are notoriously unstable and are extremely vulnerable to degradation, for example by nucleases, hydroxyl radicals, UV light, and $Mg^{2+}$-mediated inline attack. The low-stability of RNAs precludes storage for long periods of time and severely limits the potential range of distribution and application methods for RNA-based pharmaceutical compounds. As a result, RNA-based applications commonly require costly and inefficient chemical modification of RNA for stabilization and delivery.

Therefore, it is an object of the invention to provide methods and compositions for the improved delivery of RNA to a target cell or a host.

It is still another object of the invention to provide methods and compositions for down-regulating gene expression in a host.

SUMMARY OF THE INVENTION

A combined packing and assembly method that efficiently packs ribonucleic acid (RNA) into virus like particles (VLPs) has been developed. In an exemplary method VLPs spontaneously assemble and efficiently load specifically designed RNA in vivo. The VLPs confer stability to RNA against degradation by nucleases, hydroxyl radicals, UV light, and $Mg^{2+}$-mediated inline attack. VLPs that contain biologically active RNA have been designed, produced and tested. The RNA is loaded in the particles at a density of about three RNA molecules per viral particle. The purity of the RNA in the VLPs can be controlled by RNA sequence and length. The RNA can be designed to inhibit a target gene when introduced to a target cell or organism. For example, double-stranded RNA corresponding to the target gene can be packaged into the VLPs. The RNA-loaded VLPs are taken up by target cells, including human cells, and the interfering RNA (iRNA) machinery of the target cell cuts the double-stranded RNA into short interfering RNA (siRNA) molecules, for example into RNA fragments of about 21 to 23 consecutive nucleotides in length. The siRNA down regulates expression of the target gene (see Milhavet, et al., *Pharmacol Rev,* 55: 629-648 (2003); Agrawal et al., *Microbio. Mol. Biol. Rev*., pp. 657-685 (2003)).

The disclosed compositions and methods enable the production of VLPs that contain RNA. VLPs containing RNA are called "VLP-RNAs". VLPs protect the enclosed RNAs from chemical, photo- and enzymatic degradation. The RNA within a VLP is stabilized against degradation by nucleases, hydroxyl radicals, UV light, and $Mg^{2+}$-mediated inline attack. VLPs eliminate requirements for chemical modification to stabilize and deliver RNA and provide the ability to deliver RNA in a stable form that is readily taken up by cells. VLPs containing RNA capable of interference activity can deliver RNA targeting the expression of any gene in any organism that contains active iRNA machinery, including most eukaryotes.

In one embodiment virus like particles encapsulating ribonucleic acid (collectively referred to as VLP-RNAs) include a viral particle formed from the coat proteins of a bacteriophage and one or more RNA polynucleotides. The coat proteins encapsulate the one or more RNAs within the viral particle. The RNAs contain a nucleotide sequence with high affinity for the bacteriophage or virus coat protein to enable packaging of the RNA into the VLP. The efficiency of packaging is further controlled by the length and folding propensities of the RNA. In some embodiments RNAs contain one or more nucleotide sequences complementary to a target gene. The size of the RNA contained within the VLP can be fewer than 50 nucleotides to many kilo-bases in length.

RNAs encapsulated within VLPs can be single-stranded or double-stranded RNA (dsRNA). In some embodiments the RNAs optionally contain a nucleotide sequence that facilitates purification of the RNA by affinity chromatography. In one embodiment the nucleotide sequence that facilitates purification forms an RNA aptamer. Typically the sequence of the RNA within the VLP is derived from eukaryotic mRNA or ncRNA. The RNA can be single- or double-stranded. In other embodiments, the RNA is not a naturally occurring RNA. In some embodiments the RNA contains thermal-stable tetraloops, G-quartets and other motifs that confer desired folding propensities.

In one embodiment the RNA within the VLP is a precursor RNA capable of producing iRNA that inhibits expression of a target gene. Exemplary iRNAs include micro RNA (miRNA) and short interfering RNA (siRNA) (see, for example, Zeng, et al., *PNAS,* 100:9779-9784 (2003)). Typically the target gene is a eukaryotic gene. In some embodiments the virus coat protein is the q beta coat protein. In one embodiment the RNA is packaged within the VLPs at an RNA/VLP molar ratio of about 3.6.

A bacterial cell producing VLPs that contain RNA is also provided. In one embodiment the bacterial cell is an *Escherichia coli* cell. In some embodiments the RNA and the VLP genes are encoded by the same expression construct. In one embodiment the expression of the VLP genes and RNA are under the control of the same promoter. In another embodiment the expression of the VLP genes and the RNA are under the control of different promoters. The one or more promoters can optionally be inducible promoters.

Methods for the in vivo expression and packaging of RNA within VLPs are also included. Typically the methods include engineering a recombinant host cell, for example a bacterial cell, to express one or more genes encoding one or more RNAs of a target gene or a complement RNA thereof. The one or more RNAs are engineered to contain a high affinity tag for a bacteriophage or virus coat protein. The recombinant host cell is engineered to also express one or more genes encoding the coat protein of a bacteriophage corresponding to the recognition tag within the RNA. The methods also include expressing the RNA and coat protein constructs in the cells as well as purifying the resulting VLPs containing RNA.

A kit for the in vivo production of VLPs containing RNA is also described. Typically, the kit includes containers housing one or more expression vectors for the expression of RNA and virus like particles within *Escherichia coli*. One of the expression vectors contains one or more genes encoding the coat protein of a bacteriophage or virus. One of the expression vectors contains an expression cassette for the expression of the RNA. In some embodiments the expression cassette contains a multiple cloning site for the incorporation of a nucleotide sequence complementary to that of the desired target. The multiple cloning site is located directly downstream of a sequence with high affinity for the bacteriophage or virus coat protein. The expression cassette enables production of a RNA containing both the desired target sequence and the sequence with high affinity for the coat protein. In one embodiment each container vessel contains a defined quantity of a single expression vector.

BRIEF DESCRIPTION OF THE DRAWINGS

FIGS. 2A, 2C, and 2E are denaturing polyacrylamide gels of naked RNA and VLP-packaged RNA for different time intervals. FIGS. 2B, 2D, and 2F are bar graphs showing the major RNA band level expressed as a percentage of the initial value was plotted versus time with different treatment for each of the denaturing polyacrylamide gels. Naked RNA and VLP-packaged RNA are treated (FIGS. 2A-2B) Hydroxyl radical cleavage: samples were treated with free hydroxyl radicals that were created from the Fenton reaction., (FIGS. 2C-2D) Metal ion-based cleavage: samples were treated with 150 mM $Mg^{2+}$ ions at 37° C., (FIGS. 2E-2F) Spontaneous degradation: samples were treated without $Mg^{2+}$ ions at 37° C.

FIGS. 5A-5D are fluorescent photomicrographs showing suppression of gene expression using VLP-pre-miRNA: The in vivo VLP-packaged pre-miRNA knocks down the GFP gene expression in HeLa cells. The pre-miRNA designed to knock down the GFP gene expression is packed by the production of VLP simultaneously in vivo. Prior to the incubation of the in vivo VLP-packaged pre-miRNA with HeLa cells, the GFP gene was first chemically transfected into HeLa cells. The GFP gene expression level was then observed by using fluorescence microscopic techniques. The HeLa cells are treated with (FIG. 5A) as control, no GFP gene transfection, (FIG. 5B) the GFP gene transfection, (FIG. 5C) the in vivo VLP-packaged miRNA after the GFP gene transfection, and (FIG. 5D) the wild type VLP contains no designed pre-miRNA after the GFP gene transfection. The images were taken for each condition setup after 24 hours. The VLP concentration is 1 uM. In the images, white spots show the GFP gene expressions.

DETAILED DESCRIPTION OF THE INVENTION

I. Definitions

Figure 1:
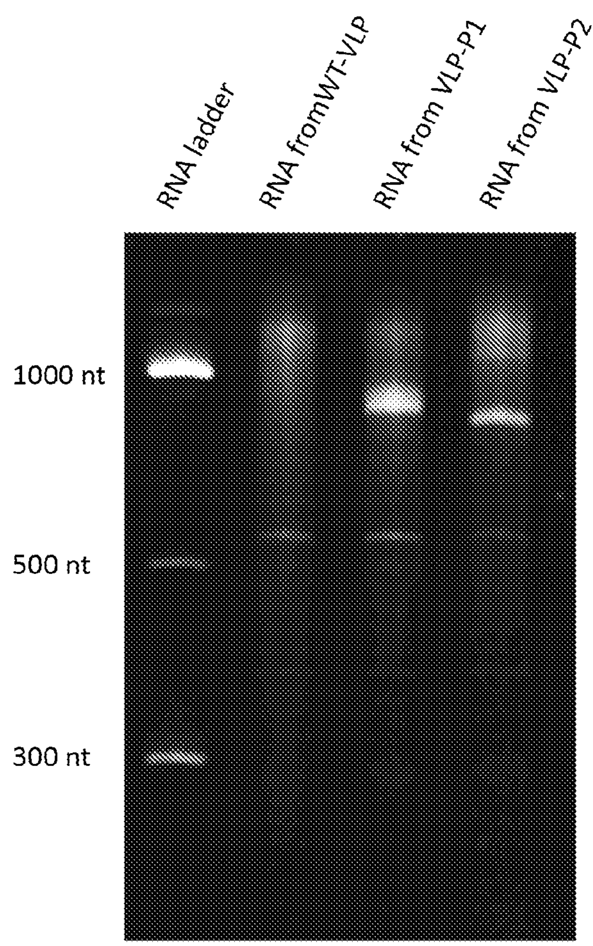
FIG. 1 is an image of a denaturing polyacrylamide gel of RNA which was packaged into a VLP by co-expression of the capsid protein and the RNA in vivo. The most intense band in the lane labeled "product RNA" corresponds to the packaged RNA including the duo tags, which is 751 nucleotides in length. mRNA encoding the capsid protein is shown as the faint band in the left lane below the position of the 650 nt size marker band. The single band corresponding to 650 nucleotides is the shown in the lane on the right.

The term "host cell" refers to prokaryotic and eukaryotic cells into which a recombinant expression vector can be introduced.

The terms "transformed" and "transfected" encompass the introduction of a nucleic acid (e.g., a vector) into a cell by a number of techniques known in the art.

The term "specifically binds" to a target refers to a binding reaction which is determinative of the presence of the molecule in the presence of a heterogeneous population of other biologics.

"Localization Signal" or "Localization Sequence" or "Recognition Sequence" or "Targeting Signal" or "Recognition Sequence" or "Recognition Tag" or "Recognition polynucleotide" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location.

The term "vector" refers to a replicon, such as a plasmid, phage, or cosmid, into which another DNA segment may be inserted so as to bring about the replication of the inserted segment. The vectors described herein can be expression vectors.

The term "expression vector" refers to a vector that includes one or more expression control sequences.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "iRNA" refers to a ribonucleic acid (RNA) molecule which can bind by complementary base pairing to a target messenger RNA transcripts (mRNAs), usually causing translational repression or target degradation which results in gene silencing reduced gene expression. Exemplary iRNA molecules include but are not limited to short interfering RNA (siRNA) and micro RNA (miRNA).

The terms "target gene" and "target sequence" are used interchangeably and refer to a sequence that can hybridize with an iRNA and induce gene silencing.

The terms "individual," "individual," "subject," and "patient" are used interchangeably herein, and refer to a mammal, including, but not limited to, humans, rodents, such as mice and rats, and other laboratory animals.

The terms "virus like particle", or "VLP" refer to a viral capsid formed from the assembly of viral coat proteins, that does not contain any viral genetic material. A "VLP-RNA" is a recombinant virus like particle containing a capsid of viral or bacteriophage coat proteins and one or more RNA molecules enclosed within the capsid.

II. Compositions for Delivery of RNA

Virus-like particles (VLPs) represent a promising delivery vehicle for RNAs. VLPs are symmetric, multi-protein structures that self-assemble into 100 nm-scale particles with virus-like morphology. Compositions for the delivery of RNA which employ VLPs as vessels containing RNA cargo are disclosed for a range of applications, including therapeutics, agriculture, the development of biofuels and as tools for basic research.

A. RNAs Capable of Interference Activity

RNA is a biological polymer with key roles in transcription, translation and many other biological functions. Over the last several decades RNA has been found to play a variety of regulatory roles in gene expression. An RNA polynucleotide with interference activity of a given gene will down-regulate the gene by causing degradation of the specific messenger RNA (mRNA) with the corresponding complementary sequence and preventing the production of protein (see Sledz and Williams, *Blood,* 106(3):787-794 (2005)). When an RNA molecule forms complementary Watson-Crick base pairs with an mRNA, it induces mRNA cleavage by accessory proteins. The source of the RNA can be viral infection, transcription, or introduction from exogenous sources.

VLPs that contain RNA designed for RNA interference activity are disclosed. VLPs containing RNA offer several advantages over traditional RNA synthesis, packaging and delivery methods. Specifically, in vivo synthesis of VLPs containing RNA in *Escherichia coli* is cost-effective, adaptable and reliable.

B. Virus-Like Particles (VLPs)

Virus-like particles (VLPs) are symmetric, multi-protein structures that self-assemble into 100 nm-scale particles with virus-like morphology. On their exterior, VLPs resemble bacteriophages and viruses, but internally, VLPs can lack native genomic material (RNA or DNA required for integration, reverse transcription, replication, infection, etc.). Mutations and chemical modifications of VLP surfaces confer a variety of chemical and physical properties to VLPs. VLPs can be engineered as nano-containers that protect and deliver 'cargo' such as RNA.

It is known that self-assembly of VLPs can follow naturally from expression of viral envelope, capsid or coat proteins. A variety of small molecule and macromolecular cargo can be incorporated into a VLP without influencing the external morphology.

C. VLPs Containing RNA

VLPs are disclosed for the packaging, protection and delivery of one or more RNA molecules within a viral capsid vessel. Virus like particles containing RNA are called "VLP-RNAs". RNA can be engineered to be packaged within VLPs for the production of VLP-RNAs in a single-step process (FIG. 1), according to the disclosed compositions and methods.

1. Design of RNA for Incorporation into VLPs

RNAs are designed for use in a simple in vivo system (in *Escherichia coli*) that spontaneously produces and packages the RNA into VLPs.

To provide RNA for incorporation within VLPs, one or more genes are built by recursive PCR or are cloned from a cDNA or genomic library. Methods and techniques for the production and design of cDNA are known in the art (see, for example, Bowman, et al., Recombinant and in vitro RNA synthesis: Methods and protocols, methods in molecular biology, Conn G L, editor. Springer Science, LLC. pp: 19-41 (2012)).

Typically the RNA includes a sequence complimentary to a target gene within a target organism, a viral coat protein recognition tag and optionally an additional sequence or tag for purification. The viral coat protein recognition tag facilitates the efficient and spontaneous uptake and assembly of the RNA into VLPs. In some embodiments the RNA is double stranded RNA. For the production of dsRNA, an expression vector is designed to include the DNA template from which both strands of RNA are to be derived.

a. RNA Stability

Production, packaging, storage and delivery of RNA remains the central challenge to the therapeutic application of RNAi technology. Purified RNAs are notoriously unstable and are extremely vulnerable to degradation, for example by nucleases, hydroxyl radicals, UV light, and $Mg^{2+}$-mediated inline attack. The low-stability of RNAs precludes storage for long periods of time and severely limits the potential range of distribution and application methods for RNA-based pharmaceutical compounds. As a result, RNA-based applications commonly require costly and inefficient chemical modification of RNA for stabilization and delivery. As we show in FIG. 2, RNA is protected by VLPs from unfavorable conditions: Denaturing polyacrylamide gel analysis of naked RNA and VLP-packaged RNA for different time intervals shows that the VLPs protect the RNA. Hydroxyl radical cleavage, metal ion-based cleavage (inline cleavage, and spontaneous degradation are all severely attenuated by packaging in VLPs.

b. Gene Targeting

Figure 3:
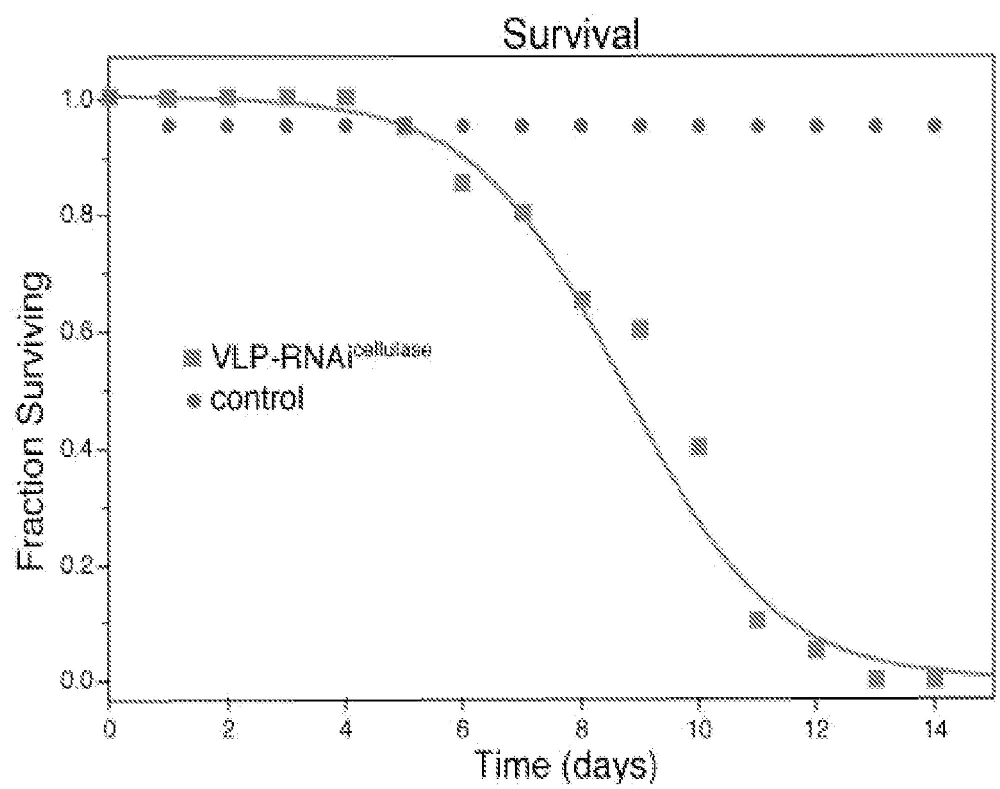
FIG. 3 is a scatter dot plot to illustrate the survival of the Eastern subterranean termite *Reticulitermes flavipes* (as a fraction of the starting quantity), over time (in days), for termites consuming filter paper containing 600 μg VLP-sRNA (■) or a control containing buffer (●), respectively.

DNA templates can be designed to express RNAs that have interfering activity against a specific target gene within a specific target organism (FIG. 3.) In some embodiments the target organism is a eukaryotic organism, such as a plant, animal, alga or fungus. Typically the target gene is not a naturally occurring viral gene.

In some embodiments the RNA can induce sequence-specific silencing of the expression or translation of the target polynucleotide, thereby down-regulating or preventing gene expression. In one embodiment the RNA can induce the complete lack of expression of the target gene. In another embodiment the RNA can reduce the level of expression of the target gene below that of an untreated control.

In some embodiments the RNA polynucleotide is a double-stranded small interfering RNA (siRNA). Typically, small interfering RNAs are between 21 and 23 nucleotides in length. The siRNAs can be expressed within the host cell.

In other embodiments the RNA polynucleotide is a micro RNA (miRNA). A miRNA is a small RNA that adopts a hairpin conformation. The miRNA can be cleaved into biologically active dsRNA within the target cell by the activity of the endogenous cellular enzymes, for example the enzyme Dicer and Dicer-like enzymes.

In some embodiments the RNA polynucleotide is a long double stranded RNA molecule (dsRNA) that is at least 24 nucleotides in length. The dsRNA is processed into a biologically active siRNA or 21-23 nucleotides by the activity of the endogenous cellular enzymes, for example the enzyme Dicer and Dicer-like enzymes within the target organism. The dsRNA contains a nucleotide sequence that is complimentary to one or more genes that are to be targeted for down-regulation.

The one or more target genes can be of any desired sequence. In some embodiments the sequence of the RNA is 100% complementary to the sequence of the target gene. In other embodiments the RNA is less than 100% complementary to the target gene. In certain embodiments the RNA is at least 95%, at least 90%, at least 85% or at least 80% complementary to the nucleotide sequence of the target gene, so that sequence variations that can occur, for example due to genetic mutation, evolutionary divergence and strain polymorphism can be tolerated.

The size of RNA contained within the VLP can be fewer than 50 nucleotides to many kilo-bases in length.

The results of confocal laser scanning microscopy indicate the spontaneous uptake of undecorated VLPs by mammalian cells (HeLa cells). This is the first demonstration of uptake by human cells of undecorated Qβ VLPs, although uptake has been demonstrated for MS2 (Stockley, 2013). Spontaneous Qβ VLP uptake is fast (FIG. 4), plateauing between 24 and 48 hours, which is roughly similar to what was observed for MS2.

VLP-RNA interference of gene expression in vivo. Our lab designed and constructed a new RNA expression vector that generates hybrid pre-miRNA (hpmiRNA) directed against Green Fluorescent Protein (GFP) expression (FIG. 5). These VLP-hpmiRNAs were produced and assembled in vivo, (in *E. coli*) and isolated. VLP-hpmiRNAs were used to treat HeLa cells that were expressing GFP. The hpmiRNA was released in the HeLa cells and efficiently down-regulated GFP expression. We have used fluorescence microscopy to show the difference of GFP expression between treated and untreated HeLa cells. According to the quantitative analysis by flow cytometry (FIG. 6), the concentration of VLP-hpmiRNA required to inhibit 50% of GFP expression in HeLa cells is 335 nM in 24 hours, and 100 nM in 48 hours (FIG. 7). The results indicate that the efficiency of VLP-hpmiRNA is high and is both concentration and time dependent. In control experiments high concentration of WT-VLP (without pre-miRNA) did not show any inhibition of target gene expression. We claim that VLP-hpmiRNAs function as controlled release capsules to release pre-miRNA steadily and continuously over time. This unique feature could extend the time course of the suppression of target gene expression compared with conventional RNAi technology.

c. Coat Protein Recognition Tag

RNA that is designed for incorporation within VLPs contains a sequence that is a recognition tag for the bacteriophage or virus coat protein of the VLP. Typically the recognition tag facilitates efficient packaging of the RNA into the VLP. Recognition tags for viral and bacteriophage coat proteins are known in the art and include, but are not limited to the q beta bacteriophage coat protein (See, for example, Witherell, et al., *Biochemistry,* 28:71-76 (1989)), the PP7 coat protein (see Lim and Peabody, *Nucleic Acids Res.,* 30 (19) 4138-4144 (2002)). In one embodiment the recognition tag is a 54-nucleotide RNA containing two hairpin structures specific for the enterobacteria bacteriophage q beta coat protein. The sequence of the tag (SEQ ID NO. 1) is 5' rUUCCUCGUGCUUAGUAACUAAGGAUGAAAUG CAUGUCUAAGACAGCAUCUUCGC 3' d. Sequence for RNA Purification

If necessary, the RNA is designed to include a sequence to assist the purification of the RNA. In some embodiments the sequence forms an RNA aptamer. RNA aptamers can assist in the purification of the RNA through affinity chromatography with RNA binding proteins. In one embodiment a sequence (taken from prior art: *Nucleic Acids Research,* 2001, VO1.29, No. 2 e4) that assists in the purification of the RNA is located at the opposite end of the RNA polynucleotide to the bacteriophage or viral coat protein recognition tag. The sequence of the RNA tag (SEQ ID NO. 2) is 5' CAGCAAGUUCCGCAACCGUA UCAAAACGUAAAUUACUCGGAC 3'

2. Viral Coat Protein

VLP-RNAs include bacteriophage or viral coat proteins. Viral or bacteriophage coat proteins are known in the art and include the enterobacteria bacteriophage Q beta coat protein and the bacteriophage PP7 coat protein. An exemplary nucleotide sequence for genes encoding the bacteriophage Q beta coat protein is

```
 46  atggc aaaattagag
 61  actgttactt taggtaacat cgggaaagat ggaaaacaaa ctctggtcct caatccgcgt
121  ggggtaaatc ccactaacgg cgttgcctcg ctttcacaag cgggtgcagt tcctgcgctg
181  gagaagcgtg ttaccgtttc ggtatctcag ccttctcgca atcgtaagaa ctacaaggtc
241  caggttaaga tccagaaccc gaccgcttgc actgcaaacg gttcttgtga cccatccgtt
301  actcgccagg catatgctga cgtgaccttt tcgttcacgc agtatagtac cgatgaggaa
361  cgagcttttg ttcgtacaga gcttgctgct ctgctcgcta gtcctctgct gatcgatgct
421  attgatcagc tgaacccagc gtattga
```

(from SEQ ID NO. 3). GenBank: M99039.1.

An exemplary amino acid sequence for the bacteriophage Q beta coat protein gene is

```
        10         20         30         40
MAKLETVTLG NIGKDGKQTL VLNPRGVNPT NGVASLSQAG

        50         60         70         80
AVPALEKRVT VSVSQPSRNR KNYKVQVKIQ NPTACTANGS

        90        100        110        120
CDPSVTRQAY ADVTFSFTQY STDEERAFVR TELAALLASP

       130
LLIDAIDQLN PAY
```

(SEQ ID NO. 4).

II. Methods for Making and Using VLPs Containing RNA

Methods for the production of VLPs containing RNA are provided. Methods for the purification and delivery of the VLPs containing RNA are also provided.

A. Production of VLPs Containing RNA

Methods for single-step production of VLPs containing RNA are disclosed. The methods can be used, for example, for the production and packaging of RNA into VLPs. Typically, the expression of RNA is greater in the prokaryotic expression system when the RNA is sequestered and packaged into VLPs than when RNA is produced alone. The RNA and VLPs self-assemble with high specificity into "VLP-RNAs" when the RNA is fused the appropriate tag (for example, an RNA hairpin sequence). The methods do not impose any limitation on the structure of the RNA that is to be packaged within the VLPs. VLP packaged RNAs can be long or short, single-stranded or double-stranded, and can be of any sequence.

The purification of VLPs containing RNA produced by the disclosed methods is trivial, and is simpler than the purification of unpackaged RNA. VLPs protect the enclosed RNAs from chemical, photo- and enzymatic degradation. The RNA in a VLP is stabilized against degradation by nucleases, hydroxyl radical, UV light, and $Mg^{2+}$-mediated inline attack. VLPs eliminate requirements for chemical modification to stabilize and deliver RNA. The high-stability of VLP-RNAs enables storage for long periods of time and allows for a broad range of application methods, including distribution as aerosols, solutions, powders, etc. The VLP-RNAs are readily taken up by many cell types and efficiently deliver RNA to biological targets. Furthermore, production and usage of VLPs containing RNA is water-based and environmentally sound. RNA within VLP is stable indefinitely at room temperature. [We are doing a lot of experiments to characterize RNA stability under extreme conditions (Temp, UV, etc) and can add a subsection on this later]

1. Expression of VLP Genes and RNA

For the expression of VLPs and RNA, the host organism is transformed with plasmids that express genes for the coat protein of a bacteriophage or virus in addition to one or more RNA gene(s).

Typically, the gene(s) encoding RNA and genes encoding bacteriophage or viral coat proteins are cloned into an expression system for the expression of VLPs containing RNA in vivo. Suitable expression systems are known in the art (see, for example, Studier, *Protein Expr Purif,* 41: 207-234. (2005)). The coat protein is expressed in the pCDF-1b expression vector. The RNA is expressed in either pET-28b or pUC-19.

In some embodiments, the in vivo expression of RNA occurs in a prokaryote. Prokaryotes commonly utilized for the expression of RNA include, but are not limited to bacteria such as *Escherichia* spp., *Bacillus* spp. and *Thermophilus* spp. In one embodiment the host organism for in vivo production of VLPs containing RNA is *Escherichia coli*. Useful *Escherichia coli* strains for expressing and producing polypeptides are well known in the art. The BL21(DE3) strain of *E. coli* is used to express the protein and RNA.

Expression cassettes that are designed for the expression of RNA can be easily transferred to a transformation vector for transfer to the host organism and transformation techniques are well known in the art. The one or more genes encoding RNA and the one or more genes encoding the coat protein of a bacteriophage or virus can be encoded within the same expression construct, or may be encoded within two or more different expression constructs. The genes can be under the control of the same or different promoter elements. In some embodiments the expression of the VLPs containing RNA is under the control of an inducible promoter. An exemplary inducible promoter is the Isopropyl-β-D-thiogalactopyranoside (IPTG) inducible promoter.

2. Assembly of VLPs Containing RNA

The disclosed methods provide one or more RNA genes and viral or bacteriophage coat proteins that spontaneously assemble in vivo into intact "VLP-RNAs". The RNA and VLPs self-assemble with high specificity into VLP-RNAs when the RNA is fused to the appropriate tag (for example, an RNA hairpin sequence). In one embodiment, VLPs containing RNA are expressed in high yield in *Escherichia coli* cells.

In one embodiment the RNA packaged within the VLP is at least 80% pure. In other embodiments the RNA is at least 85% pure, at least 90% pure or at least 95% pure. Typically one VLP vessel contains at least one RNA molecule. In one embodiment the RNA is packaged within the VLPs at an RNA/VLP molar ratio of about 3.6, such that each VLP packs approximately three RNA molecules.

3. Purification of VLPs Containing RNA.

Because of their distinctive size, properties and high stability, VLPs can be easily purified from *Escherichia coli* cellular lysates. The purification of VLPs containing RNA (VLP-RNAs) produced by the disclosed methods is straightforward, and is simpler than the purification with fast protein liquid chromatography (FPLC), filtration, sedimentation, sucrose-gradient separation, affinity tag chromatography and flow-field fractionation multi-angle light scattering (FFF-MALS). In some embodiments purification of the VLPs containing RNA includes pelleting of the host organism cells. The pelleted cells or isolated VLPs can be frozen or dried for storage or distribution purposes.

4. Delivery of Purified VLPs Containing RNA

VLPs protect the enclosed RNAs from chemical, photo- and enzymatic degradation. The RNA in a VLP is stabilized against degradation by nucleases, hydroxyl radical, UV light, and $Mg^{2+}$-mediated inline attack. VLPs eliminate requirements for chemical modification to stabilize and deliver RNA. The high-stability of VLP-RNAs enables storage for long periods of time and allows for a broad range of application methods, including distribution as aerosols, solutions, powders, etc. The VLPs are readily taken up by many cell types and efficiently deliver RNA to biological targets.

In one embodiment purified VLPs containing RNA are introduced into a complex eukaryotic organism by ingestion of doped food. When the VLPs are taken up by target cells, the RNA is released and the biological activity of the enclosed RNA is manifest. VLPs containing RNA can be delivered as crude cell extracts. In other embodiments they can be left within the pelleted *Escherichia coli* and delivered as intact *Escherichia coli* cells.

B. Applications of VLPs Containing RNAs

1. Therapeutics

In some embodiments VLPs containing RNA are used for the delivery of RNA for applications in therapeutics. In certain embodiments, the targeting of gene expression by the RNA is an effective therapeutic strategy against infectious disease, cancer, inflammatory disease, etc. In one embodiment, VLPs containing RNAs are used to deliver a RNA-based functional cure for hepatitis B, which infects over 300 million people world-wide.

2. Agriculture.

In some embodiments VLPs containing RNA are used for the protection of plants from weeds and insects and for increasing crop yields. In certain embodiments, the targeting of gene expression by the RNA enables the production of allergy-free peanuts and decaffeinated coffee beans. In one embodiment, VLPs are used to deliver RNA to kill mites that parasitize honeybees.

3. Biofuels

In some embodiments VLPs containing RNAs are used for the delivery of RNA designed to substantially improve solar-driven hydrogen production by microalgae.

4. Research Tools

In some embodiments VLPs containing RNAs are used for research tools. In one embodiment the RNAs are used for the study of loss of function due to silencing of target genes by RNA, for example to assist in elucidating gene function.

EXAMPLES

Example 1

Construction of a VLP Containing RNA

Materials and Methods

RNA Design and Expression

Using Known methods, one or more genes are built by recursive PCR or are cloned from a cDNA or genomic library. The genes, along with promoters and terminators, are DNA sequences designed to express the desired RNAs. The genes can be of any desired sequence and can encode either double-stranded or single-stranded RNAs. RNAs of essentially any length and sequence can be produced in high yield in *Escherichia coli*. The RNA gene(s) are cloned into an inducible expression system.

Assembly and Purification of VLPs Containing RNA.

The RNA is designed to contain a recognition tag that confers high affinity for a bacteriophage or virus coat protein along with a known aptamer for RNA purification, if necessary. The recognition tag facilitates efficient packaging of the RNA into the VLP.

In this process, *Escherichia coli* are transformed with plasmids that express the RNA gene(s) in addition to genes for the coat protein of a bacteriophage or virus. The expressed coat protein spontaneously assembles in vivo into intact VLPs that contain RNAs (VLP-RNAs). Because of their distinctive size, properties and high stability, VLPs can be easily purified from *Escherichia coli* cellular lysates.

Delivery.

Purified VLP-RNAs can be introduced into a complex eukaryotic organism by ingestion of doped food. When the VLP-RNAs are taken up by target cells, the RNA is released and the biological activity of the RNA is manifest. VLP-RNAs can be delivered as crude cell extracts. In addition they can be left within the pelleted *Escherichia coli* and delivered as intact *Escherichia coli* cells.

Results

A simple, robust, general and adaptable in vivo system in *Escherichia coli* that produces and packages RNA into VLPs was built. An integrated process for (i) Simultaneous overproduction of RNA and a bacteriophage coat protein, (ii) in vivo self-assembly of VLP-RNAs, was designed, constructed and successfully tested.

RNA was packaged into a VLP by co-expression of the capsid protein and the RNA in vivo. The RNA, which was obtained by disruption of purified VLPs, contains a capsid binding tag along with a secondary affinity tag at a terminus for optional purification. The RNA, including the duo tags, is 751 nucleotides in length, corresponding to the brightest band in the lane on the LH side. Integration of the band intensities on the gel suggests that the RNA is 80% pure. Comparison of quantity of VLP capsid protein with encapsulated RNA indicates an RNA/VLP molar ratio of 3.6. This ratio suggests that, on average, one VLP packs about three RNA molecules (see FIG. 1).

These data demonstrate that VLP-RNAs assemble and are efficiently packaged with the tagged-RNA when both coat protein and RNA are over produced in *Escherichia coli*. VLP-RNAs, the protein and RNA components of VLP-RNAs were purified and characterized (see FIG. 1). The sequence of the RNA used in this example (SEQ ID NO. 5) is 5'

5′ rGUCCGAGUAAUUUACGUUUUGAUACGGUUGCGGAACUUGCGGGGUG
CCUAUUGAAGCAUGAGCCGGCGACUCAGCCGUAAGGCUGGACCCGAAACC
GGGCGAGCUAGCCCUGGCCAGCCGUAAGGCGAACCGGUGGGGGAUGCAAA
CCCCUCGGAUGAGCUGGGGCUAGGAGUGAAAAGCUAACCGAGCCCGGAGA
UAGCUGGUUCUGCCGUAAGGCAGCGUUGCCGUAAGGCAAGUGCGAAUGCC
GGCAUGAGUAACGAGCGGGAGAACCCUCGCCAAGGAACUCUGCAAGCCGU
AAGGCCUCUGGCGACUGUUUACCAAAAACACAGCGCCGUAAGGCGCGAGC
CGUAAGGCUAACGACCGGAGCGCUGUCUCGGCGAGGGACCCGGUGAAAUU
GAACUGGCCGUGAAGAUGCGGCCUACCCGUGGCAGGACGAAAAGACCCCG
UGGAGCUUUACUGCCGUAAGGCAGUUUGACUGGGGCGGUCGGCCGUAAGG
CUAAAAGUUACCCCGGGGAUAACAGGCUGAUCGCCGUAAGGCGGUUUGGC
ACCUCGAUGUCGGCUCGUCGCGCCGUAAGGCUUGGGCUGUUCGCCCAUUA
AAGCGGCACGCGAGCUGGGUUCAGAACGUCGUGAGACAGUUCGGUCUCUA
UCCGCCACGGGCUUCCUCGUGCUUAGUAACUAAGGAUGAAAUGCAUGUCU
AAGACAGCAUCUUCGC 3′

Example 2

VLPs Containing RNA Selectively Target and Kill Target Insects

Materials and Methods

Strategy

Delivery of RNA to a biological target using VLPs containing RNA (VLP-RNAs) and efficacy of the VLP-RNAs was demonstrated with the eastern subterranean termite *Reticulitermes flavipes* workers, an insect that causes economically significant damage to buildings and crops system in which RNA interference feeding approaches were previously shown to silence genes.

Delivery and Assay for Efficacy of VLPs Containing RNA

An active VLP-RNA was designed to selectively target the cellulose gene, a critical digestive gene of *Reticulitermes flavipes* (VLP-RNA-cellulase). A solution containing 600 μg of VLP-RNA-cellulase was added each day to filter paper and the survival of *Reticulitermes flavipes* workers consuming the VLP-RNA-cellulase doped paper was monitored throughout 14 days. A control group of termites consumed filter paper treated with buffer alone.

Results

Figures 2A, 2B, 2C, 2D, 2E, 2F:
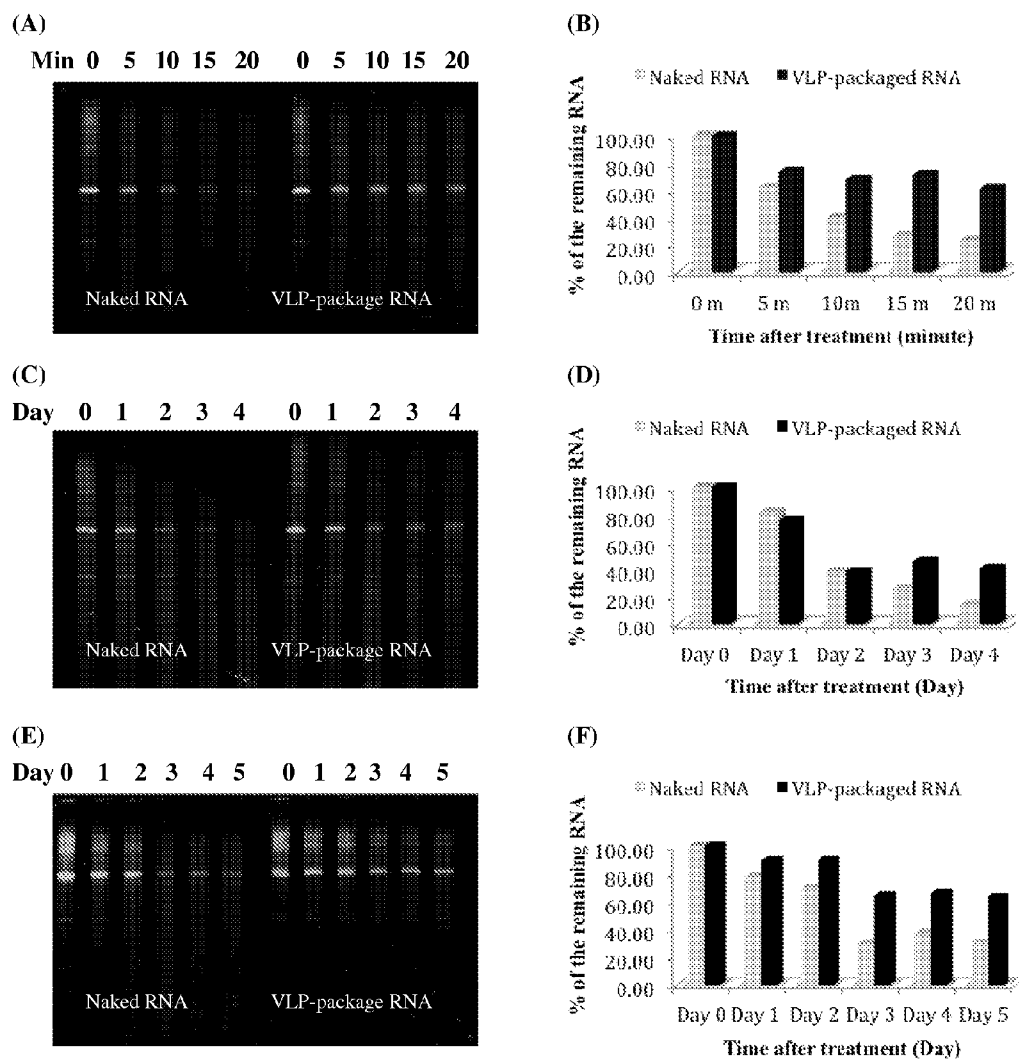
FIGS. 2A-2F show how RNA is protected by VLPs in unfavorable environments.

RNA is protected by VLPs in unfavorable environments. Denaturing polyacrylamide gel analysis of naked RNA and VLP-packaged RNA for different time intervals shown on left column (FIGS. 2A, 2C, and 2E). Major RNA band level expressed as a percentage of the initial value was plotted versus time with different treatment shown on right column (FIGS. 2B, 2D, and 2F). Naked RNA and VLP-packaged RNA are treated. Hydroxyl radical cleavage: samples were treated with free hydroxyl radicals that were created from the Fenton reaction (FIGS. 2A-2B). Metal ion-based cleavage: samples were treated with 150 mM $Mg^{2+}$ ions at 37° C. (FIGS. 2C-2D). Spontaneous degradation: samples were treated without $Mg^{2+}$ ions at 37° C. (FIGS. 2E-2F).

FIG. 3 is a scatter dot plot to illustrate the survival of the Eastern subterranean termite *Reticulitermes flavipes* (as a fraction of the starting quantity), over time (in days), for termites consuming filter paper containing 600 μg VLP-sRNA (■) or a control containing buffer (●), respectively.

Figure 4A:
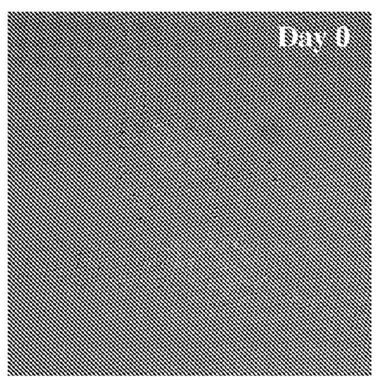
FIGS. 4A-4C are photomicrographs showing the uptake of dual-color virus like particles (VLPs) by HeLa cells: The Qβ-VLPs encapsulate the green fluorescent protein (GFP) in vitro, where the particle surface is chemically conjugated with the fluorescent dye, Dylight 633. The HeLa cells were incubated with 125 nM of [Qβ-VLP-GFP-Dylight633] at 37° C. for 0 (FIG. 4A), 1 (FIG. 4B), and 2 days (FIG. 4C). If Qβ-VLP encapsulates green fluorescent proteins and forms a complex, the co-localization will possess unique emission. Therefore, one can track GFP-loaded Qβ-VLPs using confocal laser scanning microscopy.
Figure 4B:
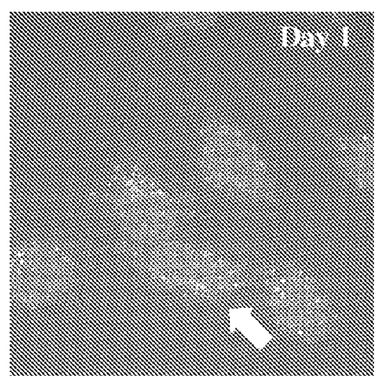
Figure 4C:
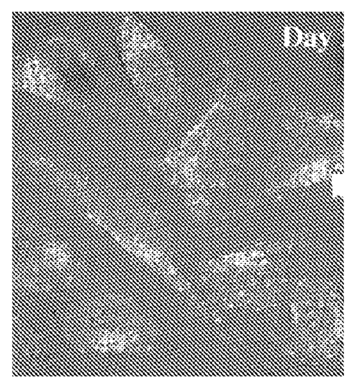

FIG. 4 shows the uptake of dual-color virus like particles (VLPs) by HeLa cells: The Qβ-VLPs encapsulate the green fluorescent protein (GFP) in vitro, where the particle surface is chemically conjugated with the fluorescent dye, Dylight 633. The HeLa cells were incubated with 125 nM of [Qβ-VLP-GFP-Dylight633] at 37° C. for 0, 1, and 2 days. If Qβ-VLP encapsidates green fluorescent proteins and forms a complex, the co-localization will possess unique emission. Therefore, GFP-loaded Qβ-VLPs were tracked using confocal laser scanning microscopy.

The in vivo VLP-packaged pre-miRNA knocks down the GFP gene expression in HeLa cells. The pre-miRNA designed to knock down the GFP gene expression is packed by the production of VLP simultaneously in vivo. Prior to the incubation of the in vivo VLP-packaged pre-miRNA with HeLa cells, the GFP gene was first chemically transfected into HeLa cells. The GFP gene expression level was then observed by using fluorescence microscopic techniques. The HeLa cells are treated with (FIG. 5A) as control, no GFP gene transfection, (FIG. 5B) the GFP gene transfection, (FIG. 5C) the in vivo VLP-packaged miRNA after the GFP gene transfection, and (FIG. 5D) the wild type VLP contains no designed pre-miRNA after the GFP gene transfection. The images were taken for each condition setup after 24 hours. The VLP concentration is 1 uM. In the images, white spots show the GFP gene expressions.

Figure 6:
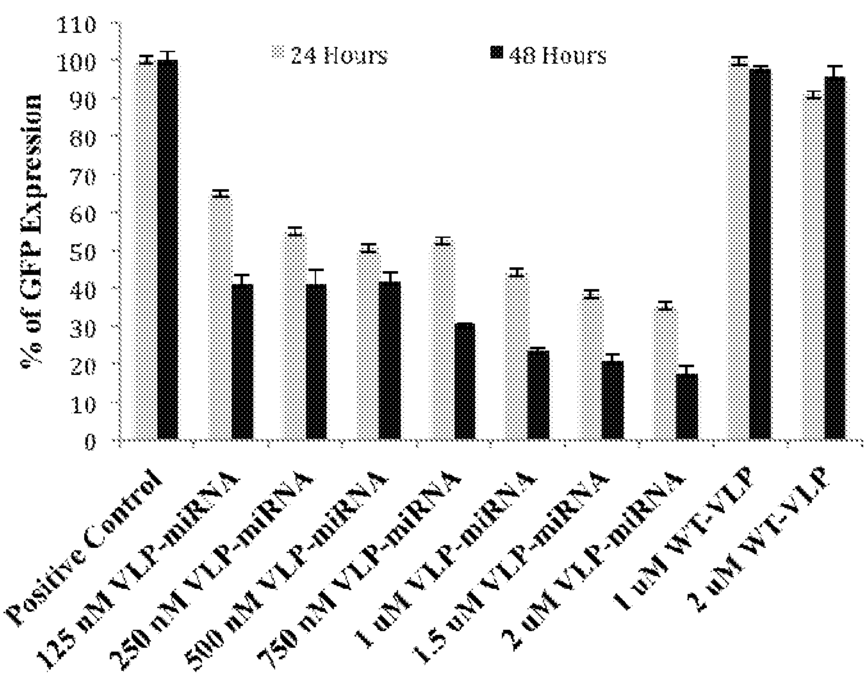
FIG. 6 is a bar graph of % GFP Expression in HeLa cells treated as indicated. Quantitation of GFP suppression in HeLa cells: The gene expression level of GFP in HeLa cells with the treatments of in vivo VLP-packaged pre-miRNA (VLP-pre-miRNA) in a concentration fashion for 24 (grey bar) and 48 (black bar) hours. The GFP gene expression levels, reported here as percentage, were analyzed by the BD LSR II Flow Cytometer. The wild type VLP (WT-VLP), which contains no designed pre-miRNA to knock down the GFP gene expression, is used to test the cell toxicity. The standard deviations (black vertical line) for each condition are shown on each bar.
Figure 7:
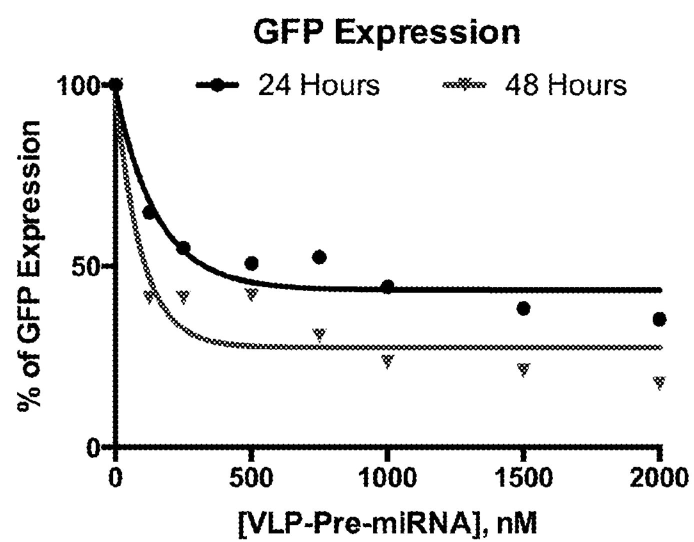
FIG. 7 is a graph showing GFP suppression (% GFP Expression) curve with VLP-packaged-pre-miRNA at 8 different concentrations (nM) up to 48 hours: Shown are one-phase decay curve models fitted to the GFP gene expression data in HeLa cells with the treatments of in vivo VLP-packaged pre-miRNA (VLP-pre-miRNA) in a concentration fashion for 24 (dot line) and 48 (inverted triangle line) hours. The concentrations for VLP-pre-miRNA to inhibit 50% of the GFP expression ($IC_{50}$) in HeLa cells are 335 nM in 24 hours, and 100 nM in 48 hours.

FIG. 6 shows the gene expression level of GFP in HeLa cells with the treatments of in vivo VLP-packaged pre-miRNA (VLP-pre-miRNA) in a concentration fashion for 24 (grey bar) and 48 (black bar) hours. The GFP gene expression levels, reported here as percentage, were analyzed by the BD LSR II Flow Cytometer. The wild type VLP (WT-VLP), which contains no designed pre-miRNA to knock down the GFP gene expression, is used to test the cell toxicity. The standard deviations (black vertical line) for each condition are shown on each bar.

FIG. 7 is a GFP suppression curve with VLP-packaged-pre-miRNA at 8 different concentrations up to 48 hours: Shown are one-phase decay curve models fitted to the GFP gene expression data in HeLa cells with the treatments of in vivo VLP-packaged pre-miRNA (VLP-pre-miRNA) in a concentration fashion for 24 (dot line) and 48 (inverted triangle line) hours. The concentrations for VLP-pre-miRNA to inhibit 50% of the GFP expression (IC50) in HeLa cells are 335 nM in 24 hours, and 100 nM in 48 hours.

VLP-RNA-cellulase acted by down-regulating expression of the critical cellulase digestive gene, and depriving the insect of nutrients causing starvation and complete mortality in the experimental group by day 13. Control termites consuming filter paper treated with buffer alone survived indefinitely (FIG. 3).

VLPs function as controlled release capsules to release pre-miRNA steadily and continuously over time. This unique feature could extend the time course of the suppression of target gene expression compared with conventional RNAi technology.

REFERENCES

1. Zeltins A (2013) Construction and characterization of virus-like particles: A review. Mol Biotechnol 53: 92-107.
2. Smith M T, Hawes A K, Bundy B C (2013) Reengineering viruses and virus-like particles through chemical functionalization strategies. Curr Opin Biotechnol.

3. Rhee J K, Hovlid M, Fiedler J D, Brown S D, Manzenrieder F, Kitagishi H, Nycholat C, Paulson J C, Finn M G (2011) Colorful virus-like particles: Fluorescent protein packaging by the q beta capsid. Biomacromolecules 12: 3977-3981.
4. Pan Y, Zhang Y, Jia T, Zhang K, Li J, Wang L (2012) Development of a microrna delivery system based on bacteriophage ms2 virus-like particles. FEBS J 279:1198-1208.
5. Lau J L, Baksh M M, Fiedler J D, Brown S D, Kussrow A, Bomhop D J, Ordoukhanian P, Finn M G (2011) Evolution and protein packaging of small molecule RNA aptamers. ACS Nano 5: 7722-7729.
6. Zhou X, Wheeler M M, Oi F M, Scharf M E (2008) RNA interference in the termite *Reticulitermes flavipes* through ingestion of double-stranded RNA. Insect Biochem Mol Biol 38: 805-815.
7. Bowman J C, Azizi B, Lenz T K, Roy P, Williams L D (2012) Preparation of long templates for RNA in vitro transcription by recursive PCR. In: Conn G L, editor. Recombinant and in vitro RNA synthesis: Methods and protocols, methods in molecular biology: Springer Science, LLC. pp. 19-41.
8. Studier F W (2005) Protein production by auto-induction in high density shaking cultures. Protein Expr Purif 41: 207-234.
9. Witherell G W, Uhlenbeck O C (1989) Specific RNA binding by q beta coat protein. Biochemistry 28: 71-76.
11. Milhavet O, Gary D S, Mattson M P (2003) RNA interference in biology and medicine. Pharmacol Rev 55: 629-648.
12. Whitehead K A, Langer R, Anderson D G (2009) Knocking down barriers: Advances in sirna delivery. Nat Rev Drug Discov 8: 129-138.
13. Oey M, Ross I L, Stephens E, Steinbeck J, Wolf J, Radzun K A, Kugler J, Ringsmuth A K, Kruse O, Hankamer B (2013) Rnai knock-down of lhcbm1, 2 and 3 increases photosynthetic h2 production efficiency of the green alga *Chlamydomonas reinhardtii*. PLoS One 8: e61375.
14. Huvenne H, Smagghe G (2010) Mechanisms of dsrna uptake in insects and potential of rnai for pest control: A review. J Insect Physiol 56: 227-235.
15. Lant B, Derry W B (2013) Methods for detection and analysis of apoptosis signaling in the *C. Elegans* germline. Methods (San Diego, Calif.) 61: 174-182.
16. Sledz and Williams, RNA interference in biology and disease, *Blood,* 106(3):787-794 (2005).
17. Zeng, Y, Rui, Y. and Cullen R., MicroRNAs and small interfering RNAs can inhibit mRNA expression by similar mechanisms, *PNAS,* 100:9779-9784 (2003)).
18. Neema Agrawal, P. V. N. Dasaradhi, Asif Mohmmed, Pawan Malhotra, Raj K. Bhatnagar, and Sunil K. Mukherjee, *Microbiology and molecular biology reviews*, pp. 657-685 (2003).

We claim:

1. A virus like particle (VLP) containing ribonucleic acid (RNA) comprising a) a virus like particle formed from coat proteins of a bacteriophage; and b) RNA comprising a capsid binding tag, wherein the capsid binding tag comprises SEQ ID NO:1;and wherein the coat proteins of the bacteriophage self-assemble to encapsidate three of the RNAs per VLP.

2. The VLP containing RNA of claim 1 wherein the RNA is processed in vivo into short interfering RNAs (siRNAs).

3. The VLP containing RNA of claim 1 wherein the bacteriophage coat protein is the bacteriophage q beta coat protein.

4. The VLP containing RNA of claim 1 wherein the VLP stabilizes the RNA against chemical, photochemical and enzymatic degradation processes.

5. The VLP containing RNA of claim 1 wherein the RNA comprises one or more selected from the group consisting of thermal-stable tetraloops, G-quartets, and triple strands.

6. The VLP containing RNA of claim 1 wherein the RNA is at least 180 nucleotides in length.

7. The VLP containing RNA of claim 1 wherein the RNA is inhibitory RNA specific for cellulase of a cellulose dependent insect.

8. The VLP containing RNA of claim 7 wherein the cellulose dependent insect is the eastern termite *Reticulitermes flavipes*.

9. The VLP containing RNA of claim 1 wherein the RNA is inhibitory RNA specific tumor-specific transcription factors.

10. The VLP containing RNA of claim 1 wherein the RNA is inhibitory RNA specific for regulators of cellular proliferation.

11. The VLP containing RNA of claim 1 wherein the target mRNA encodes proteins of infectious pathogens.

12. The VLP containing RNA of claim 1 wherein the RNA further contains a sequence tag for purification of the RNA.

13. The VLP containing RNA of claim 1, wherein the VLP is spontaneously taken up by human, insect, plant and other cells.

* * * * *

SEQUENCE LISTING

```
<160> NUMBER OF SEQ ID NOS: 5

<210> SEQ ID NO 1
<211> LENGTH: 54
<212> TYPE: RNA
<213> ORGANISM: Bacteriophage Q beta

<400> SEQUENCE: 1

uuccucgugc uuaguaacua aggaugaaau gcaugucuaa gacagcaucu ucgc          54


<210> SEQ ID NO 2
<211> LENGTH: 42
<212> TYPE: RNA
<213> ORGANISM: Bacteriophage Q beta

<400> SEQUENCE: 2

cagcaaguuc cgcaaccgua ucaaaacgua aauuacucgg ac                       42


<210> SEQ ID NO 3
<211> LENGTH: 402
<212> TYPE: DNA
<213> ORGANISM: Bacteriophage Q beta

<400> SEQUENCE: 3

atggcaaaat tagagactgt tactttaggt aacatcggga aagatggaaa acaaactctg     60

gtcctcaatc cgcgtggggt aaatcccact aacggcgttg cctcgctttc acaagcgggt    120

gcagttcctg cgctggagaa gcgtgttacc gtttcggtat ctcagccttc tcgcaatcgt    180

aagaactaca aggtccaggt taagatccag aacccgaccg cttgcactgc aaacggttct    240

tgtgacccat ccgttactcg ccaggcatat gctgacgtga ccttttcgtt cacgcagtat    300

agtaccgatg aggaacgagc ttttgttcgt acagagcttg ctgctctgct cgctagtcct    360

ctgctgatcg atgctattga tcagctgaac ccagcgtatt ga                       402
```

-continued

```
<210> SEQ ID NO 4
<211> LENGTH: 133
<212> TYPE: PRT
<213> ORGANISM: Bacteriophage Q beta

<400> SEQUENCE: 4

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130


<210> SEQ ID NO 5
<211> LENGTH: 712
<212> TYPE: RNA
<213> ORGANISM: Bacteriophage Q beta

<400> SEQUENCE: 5

guccgaguaa uuuacguuuu gauacgguug cggaacuugc ggggugccua uugaagcaug      60

agccggcgac ucagccguaa ggcuggaccc gaaaccgggc gagcuagccc uggccagccg     120

uaaggcgaac cgguggggga ugcaaacccc ucggaugagc uggggcuagg agugaaaagc     180

uaaccgagcc cggagauagc ugguucugcc guaaggcagc guugccguaa ggcaagugcg     240

aaugccggca ugaguaacga gcgggagaac ccucgccaag gaacucugca agccguaagg     300

ccucuggcga cuguuuacca aaaacacagc gccguaaggc gcgagccgua aggcuaacga     360

ccggagcgcu gucucggcga gggacccggu gaaauugaac uggccgugaa gaugcggccu     420

acccguggca ggacgaaaag accccgugga gcuuuacugc cguaaggcag uuugacuggg     480

gcggucggcc guaaggcuaa aaguuacccc ggggauaaca ggcugaucgc cguaaggcgg     540

uuuggcaccu cgaugucggc ucgucgcgcc guaaggcuug ggcuguucgc ccauuaaagc     600

ggcacgcgag cuggguucag aacgucguga gacaguucgg ucucuauccg ccacgggcuu     660

ccucgugcuu aguaacuaag gaugaaaugc augucuaaga cagcaucuuc gc             712
```